United States Patent
Fukumoto

(10) Patent No.: US 7,731,919 B2
(45) Date of Patent: Jun. 8, 2010

(54) FIXED BED REACTOR FOR GAS-PHASE CATALYTIC OXIDATION AND PROCESSES FOR PRODUCING ACROLEIN OR ACRYLIC ACID

(75) Inventor: Naohiro Fukumoto, Aioi (JP)

(73) Assignee: Nippon Shokubai Co., Ltd., Osaka (JP)

( * ) Notice: Subject to any disclaimer, the term of this patent is extended or adjusted under 35 U.S.C. 154(b) by 956 days.

(21) Appl. No.: 11/405,568

(22) Filed: Apr. 18, 2006

(65) Prior Publication Data

US 2006/0235243 A1    Oct. 19, 2006

(30) Foreign Application Priority Data

Apr. 18, 2005    (JP) .............................. 2005-120244

(51) Int. Cl.
 *C07C 51/16* (2006.01)
 *C07C 45/32* (2006.01)
 *B01J 7/02* (2006.01)

(52) U.S. Cl. .................. 422/236; 568/479; 562/545

(58) Field of Classification Search .................. None
See application file for complete search history.

(56) References Cited

U.S. PATENT DOCUMENTS

| | | | |
|---|---|---|---|
| 4,233,139 A | 11/1980 | Murrell et al. | |
| 5,182,247 A | 1/1993 | Kuhlmann et al. | |
| 5,387,720 A | 2/1995 | Neher et al. | |
| 6,395,936 B1 | 5/2002 | Arnold et al. | |
| 6,582,667 B1 | 6/2003 | Ogata et al. | |
| 6,998,504 B1 | 2/2006 | Unverricht et al. | |
| 7,456,129 B2 * | 11/2008 | Fukumoto et al. | 502/248 |

2004/0171874 A1    9/2004    Watanabe et al.

FOREIGN PATENT DOCUMENTS

| | | |
|---|---|---|
| CN | 1343190 A | 4/2002 |
| CN | 1343193 A | 4/2002 |
| EP | 0 293 224 | 11/1988 |
| EP | 0 987 057 | 3/2000 |
| JP | 6-262081 | 9/1994 |
| JP | 6-263689 | 9/1994 |
| KR | 10-2005-0024209 | 3/2005 |

OTHER PUBLICATIONS

European Search Report dated Aug. 18, 2006 issued in connection with EP Application No. 06 00 8037 corresponding to the present U.S. application.
Chinese Office Action, with English translation, issued Mar. 28, 2008 in connection with Chinese Application No. 200610073668.4 corresponding to the present U.S. application.
First Examination Report dated Sep. 1, 2009 issued in Indian Patent Application No. 340/KOL/2006 corresponding to present U.S. application.

* cited by examiner

*Primary Examiner*—Paul A Zucker
(74) *Attorney, Agent, or Firm*—Wenderoth, Lind & Ponack, L.L.P.

(57) ABSTRACT

A fixed bed reactor for gas-phase catalytic oxidation, the fixed bed reactor, comprising a reaction tube filled with a gas-phase oxidation catalyst, wherein a solid acid is placed in an end portion(s) of the reaction tube or between catalyst layers of the catalyst, or mixed in the catalyst; the solid acid is an oxide or a complex oxide containing at least one kind of element selected from the group consisting of aluminum (Al), silicon (Si), titanium (Ti) and zirconium (Zr), and has a shape of sphere, cylindrical column, cylindrical tube, star, ring, tablet or pellet; the catalyst is a complex oxide containing molybdenum (Mo) and bismuth (Bi) or a complex oxide containing molybdenum (Mo) and vanadium (V); and acid strength($H_0$) of the solid acid meets an inequality: $-5.6 \leq H_0 \leq 1.5$.

20 Claims, No Drawings

FIXED BED REACTOR FOR GAS-PHASE CATALYTIC OXIDATION AND PROCESSES FOR PRODUCING ACROLEIN OR ACRYLIC ACID

BACKGROUND OF THE INVENTION

1. Field of the Invention

The present invention relates to a fixed bed reactor for gas-phase catalytic oxidation and processes for producing acrolein or acrylic acid using the fixed bed reactor.

2. Description of the Prior Art

Fixed bed reactors in which reaction is carried out by allowing a gas containing a starting material compound to flow in a reaction tube(s) filled with a catalyst are heretofore widely used for gas-phase reaction. Examples of the fixed bed reactors used for gas-phase reaction may include multi-tubular reactors in which a catalyst is filled into many reaction tubes having a small diameter and insulated reactors in which a catalyst is filled into a single reaction tube having a great diameter. Even if any of these reactors is used, when reaction is continuously carried out, solid organic substances and carbides (these substances being hereinafter referred to collectively as the "catalyst inhibitor"), which are generated due to impurities contained in a feed gas, by-products produced by the reaction, and the like, are deposited on a catalyst to deteriorate catalyst performance and increase a pressure loss, thereby lowering the yield of a final product. Thus, it is necessary to restore the catalyst by periodically removing such a catalyst inhibitor through burning or the like.

As a method of restoring a catalyst, there is known a method in which the catalyst is taken out of the reaction tube(s) and then restored outside the reaction tube(s), but it is preferred to restore the catalyst inside the reaction tube(s) in view of working time for taking out the catalyst, re-filling the catalyst, and the like.

As a method of restoring a catalyst inside the reaction tube(s), for example, Japanese Patent Laid-open Publications No. 6-262081 and No. 6-263689 disclose methods of restoring a catalyst safely and efficiently, with the catalyst remaining filled in the reaction tube(s), by heat treatment at a prescribed temperature while allowing a mixed gas containing molecular oxygen and steam to flow in the reaction tube(s).

However, in these methods, the catalyst can certainly be restored without taking out of the reactor, but it is necessary to stop the reaction every time the catalyst is restored.

Therefore, there is required a method which makes it possible to carry out a stable continuous operation over a long period of time, not by periodically stopping the reaction and removing the catalyst inhibitor deposited on the catalyst, but by suppressing the deposition of the catalyst inhibitor itself.

SUMMARY OF THE INVENTION

Under these circumstances, it is an object of the present invention to provide a fixed bed reactor for gas-phase catalytic oxidation, which can suppress an increase in pressure loss while maintaining a high yield in the gas-phase catalytic oxidation, thereby making it possible to carry out a stable continuous operation for a long period of time; and processes for producing acrolein or acrylic acid using the fixed bed reactor.

The present inventors have extensively studied to attain the above object, and as a result, they have found that when a solid acid having a specific acid strength is placed in a gas passage containing a starting material compound and/or a produced compound in the gas-phase catalytic oxidation by the use of a fixed bed reactor having a reaction tube(s) filled with a gas-phase oxidation catalyst, an increase in pressure loss can be suppressed while maintaining a high yield, thereby making it possible to carry out a stable continuous operation for a long period of time. These findings have led to the completion of the present invention.

That is, the present invention provides a fixed bed reactor for gas-phase catalytic oxidation, the fixed bed reactor comprising a reaction tube(s) filled with a gas-phase oxidation catalyst, wherein a solid acid, of which acid strength ($H_0$) meets an inequality: $-5.6 \leq H_0 \leq 1.5$, is placed in a gas passage containing a starting material compound and/or a produced compound. In the fixed bed reactor of the present invention, the solid acid may preferably be placed in the reaction tube(s).

The fixed bed reactor of the present invention may preferably be a fixed bed reactor comprising a reaction tube(s) filled with a catalyst for producing a final product by the gas-phase catalytic oxidation of a starting material compound with molecular oxygen, or a fixed bed reactor comprising a reaction tube(s) filled with a catalyst for producing an intermediate compound by the gas-phase catalytic oxidation of a starting material compound with molecular oxygen and a reaction tube(s) filled with a catalyst for producing a final product by the gas-phase catalytic oxidation of the intermediate compound with molecular oxygen. The solid acid may preferably be at least placed on an upstream side of the catalyst in a gas flow direction or mixed in the catalyst, or the solid acid may preferably be at least placed on an upstream side of the catalyst for producing the final product in a gas flow direction, or mixed in the catalyst for producing the final product, or placed on a downstream side of the catalyst for producing the intermediate product.

The term "starting material compound" as used herein refers to a compound as a starting material to be subjected to gas-phase catalytic oxidation. The term "produced compound" as used herein refers to a compound produced by the gas-phase catalytic oxidation of a starting material compound. The term "final product" as used herein refers to an objective product finally obtained by the gas-phase catalytic oxidation of a starting material compound.

The fixed bed reactor of the present invention may be used in, for example, processes for producing acrolein or acrylic acid.

The present invention further provides processes for producing acrolein or acrylic acid, in which propylene as a starting material compound is subjected to gas-phase catalytic oxidation with molecular oxygen to produce acrolein or acrylic acid as a final product, the processes comprising using a gas-phase oxidation catalyst in combination with a solid acid, of which acid strength ($H_0$) meets an inequality: $-5.6 \leq H_0 \leq 1.5$.

In the first production process of the present invention, acrolein as a final product is produced by the gas-phase catalytic oxidation of propylene as a starting material compound with molecular oxygen. For this production, fixed bed reactors comprising a reaction tube(s) filled with a catalyst for producing a final product by the gas-phase catalytic oxidation of a starting material compound with molecular oxygen may preferably be used.

Further, in the second production process of the present invention, acrolein as an intermediate compound is produced by the gas-phase catalytic oxidation of propylene as a starting material compound with molecular oxygen and acrylic acid as a final product is then produced by the gas-phase catalytic oxidation of the acrolein as an intermediate compound with molecular oxygen. For this production, fixed bed reactors comprising a reaction tube(s) filled with a catalyst for producing an intermediate compound by the gas-phase catalytic oxidation of a starting material compound with molecular oxygen and a reaction tube(s) filled with a catalyst for producing a final product by the gas-phase catalytic oxidation of the intermediate compound with molecular oxygen may preferably be used.

The present invention further provides a method for suppressing deposition of a catalyst inhibitor(s) in a fixed bed reactor comprising a reaction tube(s) filled with a gas-phase oxidation catalyst, the method comprising placing a solid acid, of which acid strength ($H_0$) meets an inequality: $-5.6 \leq H_0 \leq 1.5$, in the fixed bed reactor for gas-phase catalytic oxidation. The solid acid may preferably be filled in an end portion of the reaction tube(s) or between catalyst layers, or mixed in the catalyst.

When the fixed bed reactor of the present invention is used, the deposition of the catalyst inhibitor can be suppressed, and therefore, an increase in pressure loss can be suppressed while maintaining a high yield, thereby making it possible to carry out a stable continuous gas-phase catalytic oxidation for a long period of time. Thus, according to the production processes of the present invention, a significant reduction in the production cost of acrolein or acrylic acid can be expected.

DETAILED DESCRIPTION THE INVENTION

The fixed bed reactor of the present invention is a fixed bed reactor for gas-phase catalytic oxidation, the fixed bed reactor comprising a reaction tube(s) filled with a gas-phase oxidation catalyst (hereinafter referred to simply as the "catalyst" in some cases), wherein a solid acid, of which acid strength ($H_0$) meets an inequality: $-5.6 \leq H_0 \leq 1.5$ (such a solid acid being hereinafter referred to simply as the "solid acid" in some cases), is placed in a gas passage containing a starting material compound and/or a produced compound (this situation being hereinafter referred to simply as "in the reactor" in some cases).

The term "fixed bed reactor" as used herein refers to a vessel in which a feed gas supplied from a gas inlet(s) of a reaction tube(s) is subjected to gas-phase catalytic oxidation in the presence of a gas-phase oxidation catalyst filled statically in the reaction tube(s) and a final product containing gas is discharged from a gas outlet(s) of the reaction tube(s). This fixed bed reactor may be a stand-alone vessel or may be a vessel incorporated into a production plant.

The fixed bed reactor of the present invention has substantially the same structure as that of ordinary reactors for gas-phase catalytic oxidation, except that a solid acid is placed in the reactor, and therefore, the structure of the fixed bed reactor is not particularly limited. Thus, the fixed bed reactor of the present invention may be, for example, either a multi-tubular reactor in which the catalyst is filled into many reaction tubes having a small diameter or an insulated reactor in which the catalyst is filled into a single reaction tube having a large diameter.

In the present invention, the acid strength ($H_0$) of the solid acid is measured by the method described below in Examples. Further, the phrase "acid strength ($H_0$) meets an inequality: $-5.6 \leq H_0 \leq 1.5$" means that the acid strength ($H_0$) of the solid acid falls within the above range, that is, the acid strength ($H_0$) of the solid acid is not lower than $-5.6$ and not higher than $1.5$. Therefore, the solid acid may be composed of one kind of solid acid having an acid strength in the above range, or may be composed of two or more kinds of solid acids having the same acid strengths ($H_0$) or different acid strengths ($H_0$), so long as these acid strengths ($H_0$) fall within the above range.

The solid acid used in the present invention is not particularly limited, so long as it has the specific acid strength. Examples of the solid acid may include (complex) oxides containing at least one kind of element selected from aluminum (Al), silicon (Si), phosphorus (P), titanium (Ti), vanadium (V), zinc (Zn), zirconium (Zr), niobium (Nb), molybdenum (Mo) and tungsten (W) Specific examples of the solid acid may include alumina, silica, titania, zirconia, silica-alumina, silica-titania, silica-vanadium oxide, silica-zinc oxide, silica-zirconia, silica-molybdenum oxide, silica-tungsten oxide, alumina-titania, alumina-vanadium oxide, alumina-zinc oxide, alumina-zirconia, alumina-molybdenum oxide, alumina-tungsten oxide, titania-zirconia, titania-tungsten oxide, zinc oxide-zirconia, zeolite, and silicon-alminophosphate. The term "(complex) oxide" as used herein refers to an oxide or a complex oxide. These solid acids may be used alone, or two or more kinds of these solid acids may also be used in combination. In these solid acids, (complex) oxides containing at least one kind of element selected from aluminum, silicon, titanium, and zirconium are preferred, and complex oxides containing aluminum and silicon are particularly preferred.

The solid acid may take the form of a mixture containing two or more kinds of the above (complex) oxides; the form in which the above (complex) oxide(s) is (are) supported on the different kind(s) of the above (complex) oxide(s); the form of a mixture of the above (complex) oxide(s) and any other solid(s); or the form in which the above (complex) oxide(s) is (are) supported on any other solid(s), so long as the solid acid taking each of these forms has the specific acid strength.

The solid acid may be prepared from starting materials containing the constituent elements of a (complex) oxide(s). For example, the solid acid as a complex oxide containing aluminum and silicon, which is included in the above (complex) oxides, can be prepared by, for example, forming a mixture of alumina powder, alumina sol, and colloidal silica into a desired shape, followed by calcination. In this case, the total amount of alumina powder and alumina sol is not smaller than 60 parts by mass and not greater than 97 parts by mass, preferably not smaller than 70 parts by mass and not greater than 95 parts by mass, and more preferably not smaller than 80 parts by mass and not greater than 90 parts by mass, relative to 100 parts by mass of the total amount of alumina powder, alumina sol, and colloidal silica. The amount of colloidal silica to be mixed is not smaller than 3 parts by mass and not greater than 40 parts by mass, preferably not smaller than 5 parts by mass and not greater than 30 parts by mass, and more preferably not smaller than 10 parts by mass and not greater than 20 parts by mass, relative to 100 parts by mass of the total amount of alumina powder, alumina sol, and colloidal silica. The amount of alumina powder to be mixed is not smaller than 60 parts by mass and not greater than 97 parts by mass, preferably not smaller than 70 parts by mass and not greater than 96 parts by mass, and more preferably not smaller than 85 parts by mass and not greater than 95 parts by mass, relative to 100 parts by mass of the total amount of alumina powder and alumina sol. The amount of alumina sol to be mixed is not smaller than 3 parts by mass and not greater than 40 parts by mass, preferably not smaller than 4 parts by mass and not greater than 30 parts by mass, and more preferably not smaller than 5 parts by mass and not greater than 15 parts by mass, relative to 100 parts by mass of the total amount of alumina powder and alumina sol. The calcination temperature may preferably be not lower than 600° C. and not higher than 1,300° C., more preferably not lower than 650° C. and not higher than 1,200° C., and more preferably not lower than 700° C. and not higher than 1,100°

C. The calcination time may preferably be not shorter than 0.5 hours and not longer than 50 hours, and more preferably not shorter than 1 hour and not longer than 20 hours.

The method of controlling the acid strength of a solid acid is not particularly limited, so long as it is a method which can control the acid strength of a solid acid in such a manner that the solid acid has the specific acid strength. Specific examples thereof may include a method of adjusting a calcination temperature in the preparation of the solid acid and a method of changing the kind and/or ratio of constituent elements of a complex oxide.

The shape of the solid acid is not particularly limited, and the solid acid may take any shape selected. Specific examples of the shape may include those which are formed with ordinary forming machines such as tablet forming machines, extrusion forming machines, and granulating machines, including sphere, cylindrical column, cylindrical tube, star, ring, tablet, and pellet. When the size of the solid acid is too small, an increase in pressure loss may occur, and therefore, the reaction cannot be carried out efficiently in some cases. In contrast, when the size of the solid acid is too great, the deposition of the catalyst inhibitor cannot sufficiently be suppressed in some cases. Thus, the size of the solid acid may preferably be not smaller than 1 mm and not greater than 15 mm, more preferably not smaller than 2 mm and not greater than 12 mm, and still more preferably not smaller than 3 mm and not greater than 10 mm, in terms of the average diameter of the solid acid.

The amount of the solid acid to be used may appropriately be adjusted according to the kind, specific gravity, shape, and acid strength of the solid acid, as well as the kind, specific gravity, shape, and used amount of the catalyst, and therefore, the amount of the solid acid to be used is not particularly limited. When the amount of the solid acid to be used is too small, the deposition of the catalyst inhibitor cannot sufficiently be suppressed in some cases. In contrast, when the amount of the solid acid to be used is too great, the solid acid will be used more than necessary, and therefore, the cost of production may be increased. Thus, the amount of the solid acid to be used may preferably be 1:0.5 to 100, more preferably 1:2 to 50, and more preferably 1:3 to 30, in terms of the ratio (volume ratio) of solid acid:catalyst.

In the fixed bed reactor of the present invention, the location in the reactor (i.e., the location of a gas passage containing a starting material and/or a produced compound) where the solid acid is placed is not particularly limited, so long as it is a location suitable for suppressing the deposition of the catalyst inhibitor. A method of placing the solid acid in the reactor is not particularly limited, but the solid acid may preferably be placed in a reaction tube(s), of which specific examples may include forming at least one solid acid layer by filling the solid acid in an end portion(s) of the reaction tube(s) or between catalyst layers; and mixing the solid acid in the catalyst. These methods may be used alone, or two or more kinds of these methods may also be used in combination. In addition, when the solid acid is mixed in the catalyst, it can also serves as an inactive support which is usually used as a diluent for adjusting the activity of a catalyst.

In the case of fixed bed reactors comprising a reaction tube(s) filled with a catalyst for producing a final product by the gas-phase catalytic oxidation of a starting material compound with molecular oxygen, the solid acid may preferably be at least placed on the upstream side of the catalyst in a gas flow direction or mixed in the catalyst.

In the case of fixed bed reactors comprising a reaction tube(s) filled with a catalyst for producing an intermediate compound by the gas-phase catalytic oxidation of a starting material compound with molecular oxygen and a reaction tube(s) filled with a catalyst for producing a final product by the gas-phase catalytic oxidation of the intermediate compound with molecular oxygen, the solid acid may preferably be at least placed on the upstream side of the catalyst for producing the final product in a gas flow direction, or mixed in the catalyst for producing the final product, or placed on the downstream side of the catalyst for producing the intermediate compound. Further, the solid acid may be placed on other locations, for example, the upstream side of the catalyst for producing the intermediate compound in a gas flow direction, or the solid acid may be mixed in the catalyst for producing the intermediate compound.

The gas-phase catalytic oxidation carried out using the fixed bed reactor of the present invention is not particularly limited, so long as it is gas-phase catalytic oxidation in which the catalyst performance may be deteriorated with a lapse of the reaction time, particularly gas-phase catalytic oxidation in which the catalyst inhibitor, i.e., solid organic substances and carbides generated due to impurities contained in a feed gas, by-products produced during the reaction, may have adverse effects on the catalyst performance. Specific examples of the gas-phase catalytic oxidation may include various kinds of gas-phase catalytic oxidation for producing unsaturated aldehydes and/or unsaturated carboxylic acids from olefins, various kinds of gas-phase catalytic oxidation for producing unsaturated carboxylic acids from unsaturated aldehydes, and various kinds of gas-phase catalytic oxidation for producing unsaturated nitrites from olefins and ammonia.

In these kinds of gas-phase catalytic oxidation, various kinds of gas-phase catalytic oxidation for producing unsaturated aldehydes and/or unsaturated carboxylic acids from olefins and various kinds of gas-phase catalytic oxidation for producing unsaturated carboxylic acids from unsaturated aldehydes are preferred, and the gas-phase catalytic oxidation for producing acrolein from propylene and the gas-phase catalytic oxidation for producing acrolein from propylene and then producing acrylic acid from the acrolein are particularly preferred.

The catalyst to be used for gas-phase catalytic oxidation is not particularly limited, so long as it is a catalyst usually used for this kind of reaction. Specific examples of the catalyst may include complex oxide catalysts containing molybdenum (Mo) and bismuth (Bi) as essential components and complex oxide catalysts containing molybdenum (Mo) and vanadium (V) as essential components.

In these catalysts, for example, as a catalyst used in the gas-phase catalytic oxidation for producing acrolein from propylene, preferred are complex oxide catalysts expressed by formula (1):

$$Mo_aW_bBi_cFe_dA_eB_fC_gD_hO_x \qquad (1)$$

wherein Mo is molybdenum; W is tungsten; Bi is bismuth; Fe is iron; A is at least one kind of element selected from nickel and cobalt; B is at least one kind of element selected from alkali metals, alkaline earth metals, and thallium; C is at least one kind of element selected from phosphorus, arsenic, boron, and niobium; D is at least one kind of element selected from silicon, aluminum, and titanium; O is oxygen; a, b, c, d, e, f, g, h, and x mean the atomic ratios of Mo, W, Bi, Fe, A, B, C, D, and O, respectively, and meet inequalities: $2 \leq a \leq 10$, $0 \leq b \leq 10$, and when $a+b=12$, $0.1 \leq c \leq 10.0$, $0.1 \leq d \leq 10$, $1 \leq e \leq 20$, $0.005 \leq f \leq 3.0$, $0 \leq g \leq 4$, and $0 \leq h \leq 15$, respectively; and x is a numeral value determined by the oxidation states of the respective elements.

Further, as a catalyst used in the gas-phase catalytic oxidation producing acrylic acid from acrolein, preferred are complex oxide catalysts expressed by formula (2):

$$Mo_m V_n Q_q R_r S_s T_t O_y \qquad (2)$$

wherein Mo is molybdenum; V is vanadium; Q is at least one kind of element selected from tungsten and niobium; R is at least one kind of element selected from iron, copper, bismuth, chromium, and antimony; S is at least one kind of element selected from alkali metals and alkaline earth metals; T is at least one kind of element selected from silicon, aluminum, and titanium; O is oxygen; m, n, q, r, s, t, and y mean the atomic ratios of Mo, V, Q, R, S, T, and O, respectively, and meet inequalities: when m=12, $2 \leq n \leq 14$, $0 \leq q \leq 12$, $0 \leq r \leq 6$, $0 \leq s \leq 6$, and $0 \leq t \leq 30$, respectively; and y is a numeral value determined by the oxidation states of the respective elements.

As the reaction conditions for gas-phase catalytic oxidation, substantially the same reaction conditions as those for the ordinary kinds of gas-phase catalytic oxidation may be used, except that the solid acid is placed in the reactor, and therefore, the reaction conditions for gas-phase catalytic oxidation are not particularly limited.

The production processes of the present invention are processes for producing acrolein or acrylic acid, in which propylene as a starting material compound is subjected to gas-phase catalytic oxidation with molecular oxygen to produce acrolein or acrylic acid as a final product, the processes comprising using the gas-phase oxidation catalyst in combination with the solid acid, of which acid strength ($H_0$) meets inequality: $-5.6 \leq H_0 \leq 1.5$.

In the first production process of the present invention, acrolein as a final product is produced by the gas-phase catalytic oxidation of propylene as a starting material compound with molecular oxygen. For this production, fixed bed reactors comprising a reaction tube(s) filled with a catalyst for producing a final product by the gas-phase catalytic oxidation of a starting material compound with molecular oxygen may preferably be used. In these fixed bed reactors, the solid acid may preferably be at least placed on the upstream side of the catalyst in a gas flow direction or mixed in the catalyst, in which both cases, the deposition of the catalyst inhibitor on the catalyst can be suppressed.

Further, in the second production process of the present invention, acrolein as an intermediate compound is produced by the gas-phase catalytic oxidation of propylene as a starting material compound with molecular oxygen and acrylic acid as a final product is then produced by the gas-phase catalytic oxidation of the acrolein as an intermediate compound with molecular oxygen. For this production, fixed bed reactors comprising a reaction tube(s) filled with a catalyst for producing an intermediate compound by the gas-phase catalytic oxidation of a starting material compound with molecular oxygen and a reaction tube(s) filled with a catalyst for producing a final product by the gas-phase catalytic oxidation of the intermediate compound with molecular oxygen may preferably be used. In these fixed bed reactors, the solid acid may preferably be at least placed on the upstream side of the catalyst for producing the final product in a gas flow direction, or mixed in the catalyst for producing the final product, or placed on the downstream side of the catalyst for producing the intermediate product, in which all cases, the deposition of the catalyst inhibitor on the catalyst can be suppressed. Further, when the solid acid is placed on other locations, for example, at least on the upstream side of the catalyst for producing the intermediate product in a gas flow direction, or the solid acid is mixed in the catalyst for producing the intermediate product, the deposition of the catalyst inhibitor generated due to impurities in a feed gas can be suppressed.

As the reaction conditions for gas-phase catalytic oxidation, substantially the same reaction conditions as those which are usually used for the production of acrolein or acrylic acid by gas-phase catalytic oxidation may be used, except that the solid acid is placed in the reactor, and therefore, the reaction conditions for gas-phase catalytic oxidation are not particularly limited. The gas-phase catalytic oxidation may be carried out by, for example, allowing a mixed gas, as a feed gas, containing: a starting material compound at an amount of not smaller than 1% by volume and not greater than 15% by volume, preferably not smaller than 4% and not greater than 12% by volume; molecular oxygen at an amount of not smaller than 1 time and not greater than 10 times, preferably not smaller than 1.5 times and not greater than 8 times, in terms of volume ratio to the starting material compound; and an inert gas (e.g., nitrogen, carbon dioxide, steam) as a diluent, in contact with the catalyst to effect reaction at a temperature of not lower than 250° C. and not higher than 450° C., preferably not lower than 260° C. and not higher than 400° C., under a pressure of not lower than the atmospheric pressure and not higher than 1 MPa, preferably not higher than 0.8 MPa, and at a space velocity (under STP, i.e., standard temperature and pressure) of not lower than 300 h$^{-1}$ and not higher than 5,000 h$^{-1}$, preferably not lower than 500 h$^{-1}$ and not higher than 4,000 h$^{-1}$.

When the fixed bed reactor of the present invention is used in the gas-phase catalytic oxidation, an increase in pressure loss can be suppressed while maintaining a high yield, thereby making it possible to carry out a stable continuous operation for a long period of time, at least for about 8,000 hours, as demonstrated below in Examples. Therefore, according to the production processes of the present invention, acrolein and acrylic acid can be obtained efficiently in a high yield and stably.

EXAMPLES

The present invention will hereinafter be described more specifically by reference to Examples and Comparative Examples, but the present invention is not limited to these Examples. The present invention can be put into practice after appropriate modifications or variations within a range meeting the gists described above and below, all of which are included in the technical scope of the present invention.

In the following Examples 1 to 4 and Comparative Examples 1 to 3, using a fixed bed reactor having a reaction tube filled with a catalyst for producing an intermediate compound by the gas-phase catalytic oxidation of a starting material compound with molecular oxygen and a reaction tube filled with a catalyst for producing a final product by the gas-phase catalytic oxidation of the intermediate compound with molecular oxygen, some experiments of producing acrolein by the gas-phase catalytic oxidation of propylene with molecular oxygen and then producing acrylic acid by the gas-phase catalytic oxidation of the acrolein with molecular oxygen were continuously carried out for 8,000 hours. At this time, changes in total catalyst performance and increases in pressure loss were evaluated by carrying out gas-phase catalytic oxidation after various solid acids or ceramic rings having different acid strengths ($H_0$) were placed at various locations in the reactor.

<Preparation of Gas-phase Oxidation Catalyst>

Gas-phase oxidation catalysts used in the experiments, that is, a catalyst for the oxidation of propylene (this catalyst being hereinafter referred to as the "front-stage catalyst"), which is used for producing acrolein by the gas-phase catalytic oxidation of propylene with molecular oxygen, and a catalyst for the oxidation of acrolein (this catalyst being hereinafter referred to as the "rear-stage catalyst"), which is used for producing acrylic acid by the gas-phase catalytic oxidation of acrolein with molecular oxygen, were prepared according to the process described in Example 1 of Japanese Laid-open Patent Publication No. 64-63543. The compositions, excluding oxygen, of these catalysts, other than the supports, were $Co_4Fe_1Bi_1W_2Mo_{10}Si_{1.35}K_{0.06}$ for the front-stage catalyst and $Mo_{12}V_{4.6}Cu_{2.2}Cr_{0.6}W_{2.4}$ for the rear-stage catalyst, in terms of atomic ratios.

<Measurement of Acid Strength>

The acid strength ($H_0$) of a solid acid is determined as follows. When a sample to be measured is white colored, the sample is immersed in benzene, to which a benzene solution containing an acid-base indicator having a known pKa value is added, and a color change, to acidic color, of the indicator on the surface of the sample is observed. It is assumed that the acid strength ($H_0$) of the solid acid is between the greatest pKa value of the pKa values of the indicators which do not change color to the acidic color and the smallest pKa value of the pKa values of the indicators which change color to the acidic color. Further, when all of the indicators used change color to the acidic color, it is assumed that the acid strength ($H_0$) is lower than the smallest pKa value of the pKa values of the indicators, and when all of the indicators used do not change color to the acidic color, it is assumed that the acid strength ($H_0$) is higher than the greatest pKa value of the pKa values of the indicators. Indicators used for the measurement of an acid strength are as follows. Indicator name (pKa value): benzalacetophenone (−5.6), dicinnamalacetone (−3.0), and 4-benzeneazodiphenylamine (1.5).

When a sample to be measured is not white colored, first, the sample is placed in a vessel having a gas discharging line and a gas introduction line, and air is adequately discharged from the vessel. Then, an ammonia gas is introduced into the vessel, and the ammonia is adsorbed on the sample. Then, a sample temperature is increased while discharging this ammonia gas, and the ammonia gas discharged at each temperature is collected by liquid nitrogen and the amount of the collected ammonia per mass of the sample is measured. The acid strength ($H_0$) of the sample is determined from the obtained measurement value based on a calibration curve which has separately been prepared using solid acids having known acid strengths ($H_0$).

<Evaluation of Total Catalyst Performance>

The total catalyst performance was evaluated by the conversion rate of propylene and the yield of acrylic acid, both of which are defined by the following equations:

Conversion rate of propylene (%)=(mole number of reacted propylene/mole number of fed propylene)×100

Yield of acrylic acid (%)=(mole number of produced acrylic acid/mole number of fed propylene)×100

Example 1

First, 75 parts by mass of γ-alumina powder having an average particle diameter of 2 to 10 μm and 5 parts by mass of methyl cellulose as an organic binder were put into a kneader, followed by well mixing. Then, to this mixture were added 8 parts by mass (as an $Al_2O_3$ content) of alumina sol having an average particle diameter of 2 to 20 nm and 17 parts by mass (as a $SiO_2$ content) of colloidal silica having an average particle diameter of 2 to 20 nm, into which water was further put, and the mixture was well mixed to give an alumina mixture containing silica added. Then, this mixture was molded by extrusion, followed by drying and calcination at 1,000° C. for 2 hours, to give a solid acid which was composed of a complex oxide in the form of particles having an average particle diameter of 7.5 mm. The acid strength ($H_0$) of the solid acid obtained met an inequality:$-3.0 \leq H_0 \leq 1.5$.

A steel reaction tube of 25 mm in inner diameter and 3,000 mm in length (the reaction tube being hereinafter referred to as the "first reaction tube") was filled with 1.2 liters of the front-stage catalyst. Separately, a steel reaction tube of 25 mm in inner diameter and 3,000 mm in length (the reaction tube being hereinafter referred to as the "second reaction tube") was filled with 1.0 liter of the rear-stage catalyst. The above solid acid was placed in a length of 500 mm on the gas inlet side of the second reaction tube, that is, on the upstream side of the rear-stage catalyst in a gas flow direction in the second reaction tube. These two reaction tubes were connected by a steel pipe of 20 mm in inner diameter and 4,000 mm in length.

Then, a mixed gas containing 5% by volume of propylene, 10% by volume of oxygen, 25% by volume of steam, and 60% by volume of nitrogen was introduced as a feed gas into the two reaction tubes through the gas inlet of the first reaction tube at a space velocity of 2,000 $h^{-1}$ (STP), relative to the front-stage catalyst, to effect gas-phase catalytic oxidation. At this time, the reaction temperature in the first reaction tube was 325° C., and the reaction temperature in the second reaction tube was 260° C., and the pipe connecting between the two reaction tubes was kept hot at 170° C.

The gas-phase catalytic oxidation was continuously carried out for 8,000 hours, and consequently, the pressure loss at the portion of the second reaction tube, which had been filled with the rear-stage catalyst and the solid acid, became increased by 0.67 kPa, as compared with the initial stage of the reaction. In addition, as for the total catalyst performance, the conversion rate of propylene was 98% and the yield of acrylic acid was 92% in the initial stage of the reaction, whereas the conversion rate of propylene was 95% and the yield of acrylic acid was 87% after 8,000 hours.

Example 2

A fixed bed reactor was prepared in the same manner as described in Example 1, except that the calcination temperature of a solid acid was changed from 1,000° C. to 700° C. to give a solid acid, and the gas-phase catalytic oxidation was carried out under the same conditions as those used in Example 1. The results are shown in Table 1. Further, the acid strength ($H_0$) of the solid acid met an inequality: $-5.6 \leq H_0 \leq -3.0$.

Comparative Example 1

A fixed bed reactor was prepared in the same manner as described in Example 1, except that ceramic rings of 7.5 mm in diameter, of which acid strength ($H_0$) met an inequality: $H_0 > 1.5$, were placed, instead of using the solid acid, on the upstream side of the rear-stage catalyst in a gas flow direction in the second reaction tube, and the gas-phase catalytic oxidation was carried out under the same conditions as those used in Example 1. The results are shown in Table 1.

Comparative Example 2

A fixed bed reactor was prepared in the same manner as described in Example 1, except that the calcination temperature was changed from 1,000° C. to 1,400° C. to give a solid acid, and the gas-phase catalytic oxidation was carried out under the same conditions as those used in Example 1. The results are shown in Table 1. Further, the acid strength ($H_0$) of the solid acid met an inequality: $H_0 > 1.5$.

Comparative Example 3

A fixed bed reactor was prepared in the same manner as described in Example 1, except that the calcination temperature was changed from 1,000° C. to 500° C. to give a solid acid, and the gas-phase catalytic oxidation was carried out under the same conditions as those used in Example 1. The results are shown in Table 1. Further, the acid strength ($H_0$) of the solid acid met an inequality: $H_0 < -5.6$.

Example 3

A fixed bed reactor was prepared in the same manner as described in Example 1, except that the solid acid was substantially uniformly mixed in the rear-stage catalyst in the second reaction tube, instead of placing the solid acid on the upstream side of the rear-stage catalyst in a gas flow direction in the second reaction tube, and the gas-phase catalytic oxidation was carried out under the same conditions as those used in Example 1. The results are shown in Table 1. Further, the acid strength ($H_0$) of the solid acid met an inequality: $-3.0 \leq H_0 \leq 1.5$.

Example 4

A fixed bed reactor was prepared in the same manner as described in Example 1, except that the solid acid was placed on the downstream side of the front-stage catalyst in a gas flow direction in the first reaction tube, instead of placing the solid acid on the upstream side of the rear-stage catalyst in a gas flow direction in the second reaction tube, and the gas-phase catalytic oxidation was carried out under the same conditions as those used in Example 1. The results are shown in Table 1. Further, the acid strength ($H_0$) of the solid acid met an inequality: $-3.0 \leq H_0 \leq 1.5$.

acid, of which acid strength ($H_0$) met an inequality: $-5.6 \leq H_0 \leq -3.0$, was used, exhibited high yields of acrylic acid and small increases in pressure loss after 8,000 hours. In contrast, Comparative Example 1, in which the solid acid was not used, and Comparative Example 2, in which the solid acid, of which acid strength ($H_0$) met an inequality: $H_0 > 1.5$, was used, exhibited low yields of acrylic acid and great increases in pressure loss after 8,000 hours. In addition, Comparative Example 3, in which the solid acid, of which acid strength ($H_0$) met an inequality: $H_0 < -5.6$, was used, exhibited a small increase in pressure loss after 8,000 hours, but exhibited a significantly decreased yield of acrylic acid after 8,000 hours. From these facts, it is found that when the solid acid, of which acid strength ($H_0$) meets an inequality: $-5.6 \leq H_0 \leq 1.5$, is placed in the reactor, an increase in pressure loss can be suppressed while maintaining a high yield of acrylic acid, thereby making it possible to carry out a stable continuous operation for a long period of time.

The fixed bed reactor of the present invention can suppress an increase in pressure loss while maintaining a high yield in the gas-phase catalytic oxidation, thereby making it possible to carry out a stable continuous operation for a long period of time. Thus, when the fixed bed reactor of the present invention is used, it becomes possible to significantly reduce the production cost of basic chemicals, such as acrolein and acrylic acid, obtained by gas-phase catalytic oxidation, and therefore, the fixed bed reactor and the production process according to the present invention make a great contribution to the production fields and application fields of these basic chemicals.

The invention claimed is:
1. A fixed bed reactor for gas-phase catalytic oxidation, the fixed bed reactor comprising
    a reaction tube filled with a gas-phase oxidation catalyst for producing acrolein by gas-phase catalytic oxidation of propylene with molecular oxygen, wherein
    a solid acid is placed in an end portion(s) of the reaction tube or between catalyst layers of the catalyst, or mixed in the catalyst,

TABLE 1

| | Solid Acid | | Initial stage of reaction | | After 8,000 hours | | |
|---|---|---|---|---|---|---|---|
| | Location | Acid strength $H_0$ | Conversion rate of propylene (%) | Yield of acrylic acid (%) | Conversion rate of propylene (%) | Yield of acrylic acid (%) | Increase in pressure loss (kPa) |
| Example 1 | Second reaction tube Upstream side | $-3.0 \leq H_0 \leq 1.5$ | 98 | 92 | 95 | 87 | 0.67 |
| Example 2 | Second reaction tube Upstream side | $-5.6 \leq H_0 \leq -3.0$ | 98 | 91 | 96 | 87 | 0.67 |
| Comp. Ex. 1 | — | — | 98 | 92 | 87 | 77 | 10 |
| Comp. Ex. 2 | Second reaction tube Upstream side | $H_0 > 1.5$ | 98 | 92 | 89 | 80 | 5.3 |
| Comp. Ex. 3 | Second reaction tube Upstream side | $H_0 < -5.6$ | 99 | 76 | 95 | 62 | 0.67 |
| Example 3 | Second reaction tube Uniformly mixed | $-3.0 \leq H_0 \leq 1.5$ | 98 | 93 | 94 | 85 | 2.0 |
| Example 4 | First reaction tube Downstream side | $-3.0 \leq H_0 \leq 1.5$ | 99 | 92 | 94 | 84 | 4.0 |

As can be seen from Table 1, Examples 1, 3, and 4, in which the solid acid, of which acid strength ($H_0$) met an inequality: $-3.0 \leq H_0 \leq 1.5$, was used, and Example 2, in which the solid the solid acid is an oxide or a complex oxide containing at least one kind of element selected from the group consisting of aluminum (Al), silicon (Si), titanium (Ti) and zirconium (Zr), and has a shape of sphere, cylindrical column, cylindrical tube, star, ring, tablet or pellet, the catalyst is a complex oxide containing molybdenum (Mo) and bismuth (Bi), and acid strength ($H_0$) of the solid acid meets an inequality: $-5.6 \leq H_0 \leq 1.5$.

2. The fixed bed reactor according to claim 1, wherein the solid acid is placed in the reaction tube on an upstream side of the catalyst in a gas flow direction, or mixed in the catalyst.

3. A fixed bed reactor for gas-phase catalytic oxidation, the fixed bed reactor comprising a reaction tube filled with a first catalyst for producing acrolein by gas-phase catalytic oxidation of propylene with molecular oxygen and a reaction tube filled with a second catalyst for producing acrylic acid by gas-phase catalytic oxidation of acrolein with molecular oxygen, wherein a solid acid is placed in an end portion(s) of the reaction tube or between catalyst layer of the catalyst, or mixed in the catalyst, the solid acid is an oxide or a complex oxide containing at least one kind of element selected from the group consisting of aluminum (Al), silicon (Si), titanium (Ti) and zirconium (Zr), and has a shape of sphere, cylindrical column, cylindrical tube, star, ring, tablet or pellet, the first catalyst is the complex oxide containing molybdenum (Mo) and bismuth (Bi), the second catalyst is the complex oxide containing molybdenum (Mo) and vanadium (V), and acid strength ($H_0$) of the solid acid meets an inequality: $-5.6 \leq H_0 \leq 1.5$.

4. The fixed bed reactor according to claim 3, wherein the solid acid is placed in the reaction tube filled with the second catalyst on an upstream side of the second catalyst in a gas flow direction, or mixed in the second catalyst, or placed in the reaction tube filled with the first catalyst on a downstream side of the first catalyst.

5. A fixed bed reactor for gas-phase catalytic oxidation, the fixed bed reactor comprising a reaction tube filled with a gas-phase oxidation catalyst for producing acrylic acid by gas-phase catalytic oxidation of acrolein with molecular oxygen, wherein a solid acid is placed in an end portion(s) of the reaction tube or between catalyst layers of the catalyst, or mixed in the catalyst, the solid acid is an oxide or a complex oxide containing at least one kind of element selected from the group consisting of aluminum (Al), silicon (Si), titanium (Ti) and zirconium (Zr), and has a shape of sphere, cylindrical column, cylindrical tube, star, ring, tablet or pellet, the catalyst is a complex oxide containing molybdenum (Mo) and vanadium (V), and acid strength ($H_0$) of the solid acid meets an inequality: $-5.6 \leq H_0 \leq 1.5$.

6. The fixed bed reactor according to claim 5, wherein the solid acid is placed in the reaction tube on an upstream side of the catalyst in a gas flow direction, or mixed in the catalyst.

7. The fixed bed reactor according to claim 1, wherein the catalyst is a complex oxide expressed by formula (1):

$$Mo_a W_b Bi_c Fe_d A_e B_f C_g D_h O_x \quad (1)$$

wherein Mo is molybdenum; W is tungsten; Bi is bismuth; Fe is iron; A is at least one element selected from the group consisting of nickel and cobalt; B is at least one element selected from the group consisting of alkali metals, alkaline earth metals, and thallium; C is at least one element selected from the group consisting of phosphorus, arsenic, boron, and niobium; D is at least one element selected from the group consisting of silicon, aluminum, and titanium; O is oxygen; a, b, c, d, e, f, g, h, and x mean the atomic ratios of Mo, W, Bi, Fe, A, B, C, D, and O, respectively, and meet inequalities: $2 \leq a \leq 10$, $0 \leq b \leq 10$ and when $a+b=12$, $0.1 \leq c \leq 10.0$, $0.1 \leq d \leq 10$, $1 \leq e \leq 20$, $0.005 \leq f \leq 3.0$, $0 \leq g \leq 4$, and $0 \leq h \leq 15$, respectively; and x is a numeral value determined by the oxidation states of the respective elements.

8. The fixed bed reactor according to claim 3, wherein the first catalyst is a complex oxide expressed by formula (1):

$$Mo_a W_b Bi_c Fe_d A_e B_f C_g D_h O_x \quad (1)$$

wherein Mo is molybdenum; W is tungsten; Bi is bismuth; Fe is iron; A is at least one element selected from the group consisting of nickel and cobalt; B is at least one element selected from the group consisting of alkali metals, alkaline earth metals, and thallium; C is at least one element selected from the group consisting of phosphorus, arsenic, boron, and niobium; D is at least one element selected from the group consisting of silicon, aluminum, and titanium; O is oxygen; a, b, c, d, e, f, g, h, and x mean the atomic ratios of Mo, W, Bi, Fe, A, B, C, D, and O, respectively, and meet inequalities: $2 \leq a \leq 10$, $0 \leq b \leq 10$, and when $a+b=12$, $0.1 \leq c \leq 10.0$, $0.1 \leq d \leq 10$, $1 \leq e \leq 20$, $0.005 \leq f \leq 3.0$, $0 \leq g \leq 4$, and $0 \leq h \leq 15$, respectively; and x is a numeral value determined by the oxidation states of the respective elements; and the second catalyst is a complex oxide expressed by formula (2):

$$Mo_m V_n Q_q R_r S_s T_t O_y \quad (2)$$

wherein Mo is molybdenum; V is vanadium; Q is at least one element selected from the group consisting of tungsten and niobium; R is at least one element selected from the group consisting of iron, copper, bismuth, chromium, and antimony; S is at least one element selected from alkali the group consisting of metals and alkaline earth metals; T is at least one element selected from the group consisting of silicon, aluminum, and titanium; O is oxygen; m, n, q, r, s, t, and y mean the atomic ratios of Mo, V, Q, R, S, T, and O, respectively, and meet inequalities: when $m=12$, $2 \leq n \leq 14$, $0 \leq q \leq 12$, $0 \leq r \leq 6$, $0 \leq s \leq 6$, and $0 \leq t \leq 30$, respectively; and y is a numeral value determined by the oxidation states of the respective elements.

9. The fixed bed reactor according to claim 5, wherein the catalyst is a complex oxide expressed by formula (2):

$$Mo_m V_n Q_q R_r S_s T_t O_y \quad (2)$$

wherein Mo is molybdenum; V is vanadium; Q is at least one element selected from the group consisting of tungsten and niobium; R is at least one element selected from the group consisting of iron, copper, bismuth, chromium, and antimony; S is at least one element selected from alkali the group consisting of metals and alkaline earth metals; T is at least one element selected from the group consisting of silicon, aluminum, and titanium; O is oxygen; m, n, q, r, s, t, and y mean the atomic ratios of Mo, V, Q, R, S, T, and O, respectively, and meet inequalities: when $m=12$, $2 \leq n \leq 14$, $0 \leq q \leq 12$, $0 \leq r \leq 6$, $0 \leq s \leq 6$, and $0 \leq t \leq 30$, respectively; and y is a numeral value determined by the oxidation states of the respective elements.

10. The fixed bed reactor according to claim 1, wherein the solid acid is placed in the end portion(s) of the reaction tube or between the catalyst layers of the catalyst, or is mixed in the catalyst but does not support the catalyst.

11. The fixed bed reactor according to claim 3, wherein the solid acid is placed in the end portion(s) of the reaction tube or between the catalyst layers of the catalyst, or is mixed in the catalyst but does not support the catalyst.

12. The fixed bed reactor according to claim 5, wherein the solid acid is placed in the end portion(s) of the reaction tube or between the catalyst layers of the catalyst, or is mixed in the catalyst but does not support the catalyst.

13. The fixed bed reactor according to claim 3, wherein the reaction tube is filled with the first catalyst and the second catalyst.

14. The fixed bed reactor according to claim 1, wherein the amount of the solid acid is 1:0.5 to 100 in terms of the ratio (volume ratio) of the solid acid: the catalyst.

15. The fixed bed reactor according to claim 3, wherein the amount of the solid acid is 1:0.5 to 100 in terms of the ratio (volume ratio) of the solid acid: the catalyst.

16. The fixed bed reactor according to claim 5, wherein the amount of the solid acid is 1:0.5 to 100 in terms of the ratio (volume ratio) of the solid acid: the catalyst.

17. The fixed bed reactor according to claim 4, wherein the solid acid is placed in the reaction tube filled with the second catalyst on the upstream side of the second catalyst in the gas flow direction, or is mixed in the second catalyst but does not support the catalyst, or is placed in the reaction tube filled with the first catalyst on the downstream side of the first catalyst.

18. The fixed bed reactor according to claim 1, wherein the solid acid has a shape of sphere, cylindrical column, cylindrical tube, ring, tablet or pellet having an average diameter of not smaller than 1 mm and not greater than 15 mm.

19. The fixed bed reactor according to claim 3, wherein the solid acid has a shape of sphere, cylindrical column, cylindrical tube, ring, tablet or pellet having an average diameter of not smaller than 1 mm and not greater than 15 mm.

20. The fixed bed reactor according to claim 5, wherein the solid acid has a shape of sphere, cylindrical column, cylindrical tube, ring, tablet or pellet having an average diameter of not smaller than 1 mm and not greater than 15 mm.

\* \* \* \* \*